(12) United States Patent
Chen et al.

(10) Patent No.: US 6,667,428 B1
(45) Date of Patent: Dec. 23, 2003

(54) **HIGH EFFICIENCY PLANT TRANSFORMATION OF *BRASSICA OLERACEA***

(75) Inventors: Long-Fang O. Chen, Taipei (TW); Shang-Fa Yang, Davis, CA (US); Jia-Yuan Huang, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/588,245

(22) Filed: Jun. 6, 2000

(51) Int. Cl.$^7$ .................. C12N 15/82; C12N 15/84; A01H 1/00
(52) U.S. Cl. .................. 800/294; 435/468; 435/469; 800/278; 800/306
(58) Field of Search ................. 435/468, 469; 800/278, 290, 294, 306

(56) References Cited

PUBLICATIONS

I. J. Puddenphat et al., Transformation of *Brassica oleracea* L.: a critical review, Molecular Breeding 2: pp. 185–210.*
Belinda Martineau et al., Fruit–specific expression of the A. tumefaciens isopentenyl transferase gene in tomato: effects on fruit ripening and defense–related gene expression in leaves, The Plant Journal (1994) 5(1), pp. 11–19.*
Estelle Villemont et al., Role of the host cell cycle in the Agrobacterium–mediated genetic transformation of Petunia: evidence of an S–phase control mechanism for T–DNA transfer, PLANT (1997) 201: pp. 160–172.*
Hansen et al., Recent advances in the transformation of plants, Jun. 1999, trends in plant science, vol. 4, No. 6, pp. 226–231.*
Chen et al., Abstract P–11031, In Vitro Cellular & Development Biology, 35(3):63A, 1999.
Metz et al., "*Agrobacterium tumefaciens*–mediated . . . ," Plant Cell Reports, 15:287–292, 1995.
Clarke et al., "The influence of . . . ," Plant Growth Regulation, 14:21–27, 1994.
Rushing, James W., "Cytokinins Affect . . . ," HortScience, 25(1):88–90, 1990.
Gan et al., "Inhibition of Leaf . . . ," Science, 270:1986–1988, 1995.
Smart et al., "Delayed Leaf Senescence . . . ," The Plant Cell, 3:647–656, 1991.
Villemont et al., "Role of the host . . . ," Planta, 201:160–172, 1997.
Birch, R.G., "Plant Transformation . . . ," Annu. Rev. Plant Physiol. Plant Mol. Biol. 48:297–326, 1997.
Puddephat et al., "Transformation of Brassica . . . ," Molecular Breeding,, 2:185–210, 1996.
Sangwan et al., "Characterization of . . . ," Planta, 188:439–456, 1992.
Bhalla et al., "*Agrobacterium tumefaciens*–mediated . . . ," Molecular Breeding, 4:531–541, 1998.
Ainley et al., "Regulatable endogenous . . . ," Plant Molecular Biology, 22:13–23, 1993.
Metz et al., "Transgenic broccoli . . . ," Molecular Breeding, 1:309–317, 1995.
Cao et al., "Transgenic broccoli . . . ," Molecular Breeding, 5:131–141, 1999.
Li et al., "Altered Morphology . . . ," Developmental Biology, 153:386–395, 1992.
Smigocki et al., "Cytokinin–to–Auxin . . . ," Plant Physiol., 91:808–811, 1989.
Martineau et al., "Fruit–specific expression . . . ," The Plant Journal 5(1):11–19, 1994.

* cited by examiner

*Primary Examiner*—David T. Fox
*Assistant Examiner*—David H Kruse
(74) *Attorney, Agent, or Firm*—Fish & Richardson P.C.

(57) ABSTRACT

A method of introducing a nucleic acid into *Brassica oleracea* cells by enriching or selection for a plant cell population having a nuclear DNA phase of 4C; and contacting the plant cell population with a bacterium of the genus Agrobacterium to form a mixed culture, the bacterium having a T-DNA which includes the nucleic acid.

22 Claims, 2 Drawing Sheets

HIGH EFFICIENCY PLANT TRANSFORMATION OF *BRASSICA OLERACEA*

BACKGROUND OF THE INVENTION

Genetic transformation provides a useful tool for the study of gene regulation. In addition, randomly transformed plants can be screened for valuable characteristics, such as increased number or size of commercially valuable plant organs (e.g., the fruit). Agrobacterium-mediated delivery of genetic constructs into plant genomes has proven to be a highly useful vehicle for plant cell transformation and subsequent generation of transgenic plants. However, many plants appear to be resistant to Agrobacterium-mediated delivery. For these recalcitrant plants, as well as permissive plants, methods of increasing the efficiency of transformation using Agrobacterium would be of value.

SUMMARY OF THE INVENTION

The invention is based on the unexpected discovery that cell populations with a nuclear DNA phase or content of 4C are especially susceptible to Agrobacterium-mediated gene delivery, while cells with a nuclear DNA content of greater than 4C are less susceptible to Agrbbacterium-mediated gene delivery. Thus, by selecting or enriching cell populations for 4C cells, the efficiency of plant cell transformation can be increased.

Accordingly, the invention features a method of introducing a nucleic acid into plant cells by enriching a plant cell population for cells having a nuclear DNA phase of 4C, and contacting the enriched plant cell population with a bacterium of the genus Agrobacterium to form a mixed culture, the bacterium having a T-DNA which includes the nucleic acid. The invention further includes a method of introducing a nucleic acid into plant cells by selecting, from a plurality of plant cell populations, a plant cell population containing the highest proportion of cells having a nuclear DNA phase of 4C; and contacting the selected plant cell population with a bacterium of the genus Agrobacterium to form a mixed culture, the bacterium having a T-DNA which includes the nucleic acid.

The enriched or selected plant cell population does not have to be precultured, i.e., the cells harvested from a plant are not cultured, though they can be stored, before being contacted by the bacterium. The increase in transformation efficiency can be further augmented by subjecting the mixed culture to vacuum pressure (e.g., 0.1 bar to 0.8 bar of pressure) or by removing cells having a nuclear DNA phase of greater than 4C from the plant cell population. The plant cell population can be of a particular plant tissue, such as broccoli plant tissue, tissue of a peduncle, or a seedling tissue (e.g., of a hypocotyl or a cotyledon). In addition, the T-DNA can further include a kanamycin resistance gene, and the method can further include, after the contacting step, selecting for plant cells in a medium containing kanamycin (e.g., about 25 mg/l or more, 50 to 100 mg/l, or 75 mg/l kanamycin).

The invention also features a method of producing a transgenic broccoli plant, the method comprising introducing a nucleic acid into a broccoli plant cell using the methods described above, the nucleic acid having a nucleotide sequence encoding an isopentyl transferase.

As used herein, the nuclear DNA phase refers to the nuclear DNA content as a multiple of the amount of DNA expected to be present in a haploid nuclei. A nuclear DNA phase of 4C means that the nucleus of a cell contains an amount of DNA about four times the haploid amount.

The methods of the invention are useful for high efficiency transformation of plant cells, from which transgenic plants can subsequently be generated. The methods are particularly useful for transforming plant cells known to be resistant to Agrobacterium-mediated gene delivery.

Other features or advantages of the present invention will be apparent from the following detailed description, and also from the claims.

BRIEF DESCRIPTION OF THE DRAWINGS

FIG. 1A shows the T-DNA for pSG529(+), and FIG. 1B shows the T-DNA for pSG766A. LB=left border, SAG=senescence associated gene, SAG12 promoter is 2.2 kb, SAG-13-1 promoter is 1.88 kb, ipt=isopentyl transferase gene (0.7 kb), Nos-ter=nopaline synthase gene terminator (0.3 kb), NPTII=kanamycin resistance gene, RB=right border.

FIGS. 2A–2F are histograms for 3 day-old hypocotyl, 9 day-old hypocotyl, 3 day-old cotyledon, 9 day-old cotyledon, fresh peduncle, and peduncle stored at 4° C. for 3-4 weeks, respectively.

DETAILED DESCRIPTION

Figure 1A:
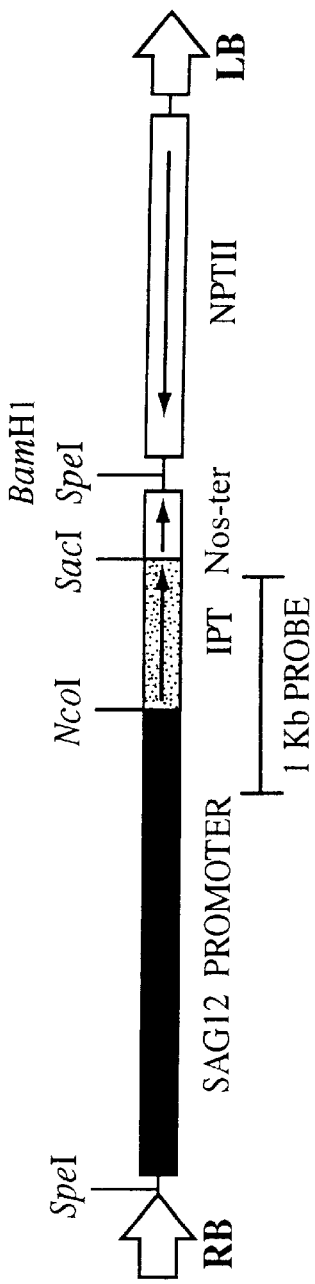
FIGS. 1A and 1B are schematic diagrams of two T-DNAs useful in the methods of the invention.

The invention relates to improved plant transformation methods using Agrobacterium-mediated gene delivery and an enrichment or selection of cells that have a nuclear DNA phase of 4C.

Plant cells vary in size and shape, nuclear volume, DNA content, and cell cycle time. Selection or enrichment for 4C cells is a feature of the invention. However, in some plant tissues, cells might not be actively dividing and are therefore resistant to regeneration or transformation. By manipulating cell growth, e.g., via the application of growth regulators or DNA synthesis inhibitors to enrich competent cells, transformation and regeneration efficiencies are increased. For example, physical and chemical methods have been used to accumulate cells in certain stage. See, e.g., Wang and Phillips, In: *Cell culture and somatic cell genetics of plant*, I. K. Vasil ed., Vol. 1, pp 175–181, 1984. Physical methods include using the cellular properties of individual cells or specifying environmental growth conditions such as light and temperature. Chemical methods include starvation of nutrient components in culture, adding growth regulators such as 2,4-D or cytokinins into culture, and adding DNA synthesis inhibitors into culture.

Plant nuclear DNA content or phase can be determined by Feulgen microspectrophotometry or laser flow cytometry, the latter having been shown to be more precise and efficient than the former (Michaelson et al., Am. J. Bot. 78:183–188, 1991; Galibraith, Science 220:1049–1051, 1983).

Another method of selecting plant cell populations with a high proportion of nuclear DNA phase 4C cells is to time the harvest of plant tissue that is to be transformed. For example, the proportion of a cell population that have a nuclear DNA phase of 4C can be monitored in various tissues of a germinating seed. As the seedling develops, the relative number of 4C cells will rise and fall. By marking the time points (e.g., relative to the beginning of germination) at which cell populations are rich in 4C cells, one can easily select 4C enriched cell populations by timing the harvesting of the tissue to be transformed. This example of enrichment can be applied to any plant tissue and at any notable time point in plant development or in vitro culture (e.g., upon induction of a cellular or biochemical event in a plant cell culture).

Alternatively, the direct physical separation of cells having a particular nuclear DNA content can be accomplished by reversible fluorescent labeling of the DNA in a plant cell population and separating the cell population based on fluorescence intensity using a flow cytometer having the ability to collect gated cells. Although the number of 4C cells selected in this manner may be relatively small, flow cytometry has the added benefit that cells having a nuclear DNA phase greater than 4C can be removed.

Without further elaboration, it is believed that one skilled in the art can, based on the above disclosure and the example described below, utilize the present invention to its fullest extent. The following example is to be construed as merely illustrative of how one skilled in the art can isolate and use the methods of the invention, and are not limitative of the remainder of the disclosure in any way. All publications cited in this disclosure are hereby incorporated by reference.

Materials and Methods

Plant material. Broccoli (*Brassica oleracea* var. italica cv. "Green King") seeds were obtained from Know-You Seed Company (Kaoshiung, Taiwan). For in vitro germination, seeds were first surface-sterilized in 70% ethanol for 1 minute, followed by 3 successive changes of 0.5% sodium hypochlorite, each change being 10 minutes long. After rinsing with sterilized water, seeds were embedded on basal MS medium (Mirashige et al., Physiol. Plant 15:473–497, 1962) without any hormone (MS0) and cultured in a growth incubator at 25° C. with a 16 hour light/8 hour dark photoperiod at a light intensity of 50–70 $\mu$mole m$^{-2}$s$^{-1}$, or alternatively in the dark only. For harvesting of floret head and peduncle, seeds were surface-sterilized and germinated directly in a vermiculite and peat-moss mixture (4:1) moistened with water. At the seeding stage showing 2 to 3 leaflets, plants were transplanted into 12-inch plots and grown in a growth chamber at 20° C. with the same photoperiod to which the plant was subjected in the growth incubator.

Agrobacterium and Plasmids. *Agrobacterium tumefaciens* strain LBA4404 harboring plasmids pSG529(+) and pSG766A containing the isopentyl transferase gene (ipt) were used in this study. See FIGS. 1A and 1B. The ipt gene is involved in cytokinin biosynthesis. Plasmids pSG529(+) and pSG766A were known to have the senescence-associated gene promoters SAG-12 (2.2 kb) and SAG-13 (1.88 kb) and the kanamycin resistance gene NPT II (neomycin phosphotransferase II). The 0.7 kb ipt gene was derived from crown gall *A. tumefaciens* (Gan et al., Science 270:1986–1988, 1995; and Lohman et al., Physiol. Plant 92:322–328, 1994).

Transformation Methodologies. Both direct co-culture and vacuum-aided infiltration of Agrobacterium-mediated transformation (Rossi et al., Plant Mol. Biol. Rep. 11:220–229, 1993) were used. For direct co-culture, explants were cut into pieces and co-incubated with plasmid-contained Agrobacterium. The bacterial concentration was about 0.8–1.0 OD$_{600}$ and diluted to 10-fold in the co-culture. After 15 minutes of co-incubation, explants were briefly washed with sterile water and cultured in medium containing 1/10 MS salt (1/10 MS0) at 25° C. under either light or dark for 3–4 days. Explants were washed by shaking in 1/10 MS0 medium containing 250 ppm cefotaxime for 3 days. The medium was replaced daily. After the 3-day incubation, the plant cells were washed in 1/10 MS0 with 500 ppm carbenicillin for one day. After this wash, explants were placed into MS medium containing vitamin B5, 2 mg/l benzyladenine, and 500 ppm carbenicillin (MSB5C500) to eliminate Agrobacterium from the culture (Gamborg et al., Exp. Cell Res. 50:151–158, 1968). After 7–10 days, explants were transferred to MSB5C500 containing 75 mg/l kanamycin sulfate for selection of transformed plant cells. Kanamycin selections were continued for at least 2 months.

For vacuum-aided infiltration, the vacuum pressure applied was 0.20 bar for both the cotyledon and hypocotyl explants and 0.68 bar for the peduncle explant. Explants in bacterial solution were vacuum-infiltrated for 10–15 minutes. After recovery to ambient pressure, explants were retained in solution for another 10–15 minutes. Treated explants were then washed with sterile water, followed by the various treatments described above. For nurses cultures, 2 ml of tobacco suspension cells (9 days after sub-culture) were laid onto an explant covered with Whatman No. 1 filter paper. The kanamycin resistant shoots obtained were rooted by transferring to MS0 medium. After rooting, plantlets were hardened in plug-plot with vermiculite and peat-moss mixture (4:1) for 2–3 weeks under 50 $\mu$mole m$^{-2}$s$^{-1}$ light. The plantlets were then transferred to 12-inch plots.

Confirmation of Transformants. For the NPT II dot assay, a small piece of leaf from each of kanamycin-resistant plantlets was assayed to exclude false positive plantlets as described in Platt et al., Anal. Biochem. 162:529–535, 1987. The extraction system and other protocols used for this assay were performed as described in Peng et al., Plant Mol. Biol. Rep. 11:38–47, 1993. Only the hybridized signals which were equivalent or stronger than the pBI121 host cell controls were considered positive.

Putative transformants were also screened using PCR and Southern hybridization. Total genomic DNA was isolated according to Chen et al., Theor. Appl. Genet. 95:1022–1043, 1997. For detection of the NPT II gene, two 21-mer primers, 5'-GAGGCTATTCGGCTATGACTG-3' (SEQ ID NO: 1) and 5'-ATCGGGAGCGGCGATACCGTA-3' (SEQ ID NO:2), were used to amplify a 0.7 kb fragment of the NPT II gene (Jun et al., Plant Cell Rep. 14:620–625, 1995). The reaction components were similar to those used in Chen et al., supra, except that 0.6 mM of each primer and 1.5 mM MgCl$_2$ was used. The thermal cycles were 94° C. for 5 minutes and then 35 cycles of 94° C. for 1 minute, 55° C. for 1 minute, and 2 minutes.

Figure 1B:
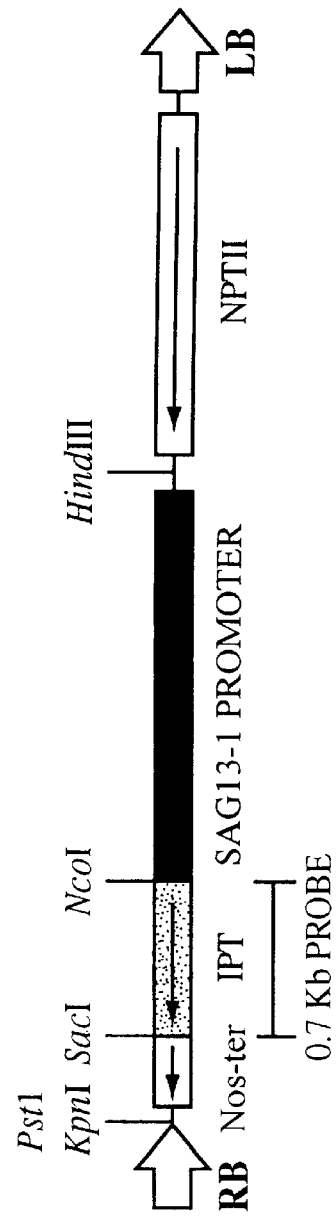

For detection of the ipt insert in pSG766A, primers 5'-ACCCATGGACCTGCATCTA-3' (SEQ ID NO:3) and 5'-GGAGCTCAGGGCTGGCGTAACC-3' (SEQ ID NO:4) (Li et al., Dev. Biol. 153:386–395, 1992) amplified a 750 bp ipt fragment, as shown in FIG. 1B. For detection of the ipt insert in pSG529(+), primers 5'-GATTTGATTAAGCTTT TAACTTGC-3' (SEQ ID NO:5) and 5'-GCCCGCCGTTG GCCTCATGAT-3' (SEQ ID NO:6) amplified a 1 kb ipt fragment, as shown in FIG. 1A. The reaction components were the same as those of NPT II amplification immediately above, except 30 mM MgCl$_2$ was used. The thermal cycles were 94° C. for 3 minutes, 55° C. for 2 minutes, and 72° C. for 3 minutes, followed by 29 cycles of 94° C. for 1 minute, 55° C. for 2 minutes, a 72° C. for 3 minutes. Agarose gel electrophoresis of the PCR products was performed as described in Chen et al., supra.

For Southern hybridization, 20 $\mu$g total genomic DNA from each transformant and non-transformant were digested with Pst I or Bam HI (3–4 U/mg DNA) and blotted onto positively-charged nylon membranes. Both ipt and NPT II fragments amplified by PCR were cut from agarose gels and extracted for dig-labeling for use in Southern hybridization. The protocols used were as described in Chen et al., supra.

Nuclear DNA Phases and Ploidy. Cell cycle/nuclear DNA phases and ploidy levels were analyzed using a flow cytometer (Elite ESP Beckman-Coulter Inc., Hong Kong) equipped with a quartz flow cell. Explants or primary leaves of transformants were mechanically chopped in Galbraith buffer (Gailbraith et al., Science 220:1049–1051, 1983) and passed through a 30 μm nylon mesh. Samples were then stained with bis-benzimide (Hoechst 33342, 1 μg/ml) and kept on ice before use. An Innova I-305 water-cooled argon laser (Coherent Inc., Santa Clara, Calif.) provided UV (333–364 nm) at 200 mW. PBS (137 mM NaCl, 2.7 mM KCl, 4.3 mM $Na_2HPO_4.7H_2O$, and 1.4 mM $KH_2PO_4$, pH 7.3) was used as a sheath buffer. Fluorescence was collected at 475–485 nm using a 488 nm band pass filter provided by the manufacture and two successive dichroic long pass filters 400 DL and 488 DL. Ploidy levels were estimated by comparing the results obtained as described immediately above with a diploid parental control.

Chlorophyll Content and Yellowing Retardation Study. Chlorophyll contents of detached leaf and floret were determined as described in Wintermans et al., Biochim. Biophys. Acta 109:448–453, 1965. Leaves from lower parts of mature plants without any symptom of yellowing were detached, while flower heads were harvested 7–14 days after beginning of bolting. Detached leaves and branches of floret heads were placed in a plastic container, covered with a transparent plastic membrane, and placed under light (16 hour light/8 hour dark) at 25° C. in a controlled room or incubator for 4 days. Chlorophyll contents were determined at days 0 and 4 and in triplicate. Chlorophyll was extracted with 96% ethanol from leaves and florets at 25° C. in darkness for over 18 hours. The absorption of the chlorophyll solution was then measured at 649 and 665 nm. Total chlorophyll content in μg/ml was calculated as $6.1 \times A_{665} + 20.04 \times A_{649}$. Absorption at 665 nm correlates with chlorophyll A content, and absorption at 649 nm correlates with chlorophyll B content. Visible changes in yellowing were also documented using a MDS 120 system (Kodak Digital Science, Eastman Kodak). The percent chlorophyll loss 4 days after storage at 25° C. was also recorded.

Results

Plant Transformation. Cytokinin-synthesizing ipt gene transformants were obtained from cotyledon, hypocotyl, and peduncle explants of broccoli using *Agrobacterium tumefaciens*-mediated transformation. Two plasmids pSG529(+) and pSG766A containing a senescence-associated gene (SAG) promoter and the kanamycin resistant NPT II gene were used as the delivery vehicles. From observations of the progeny plantlets, it was likely that most of the regenerated plantlets were directly produced from organogenesis regardless of explant sources. Multi-shooting tended to occur more frequently in peduncle explants than in cotyledon or hypocotyl. Various strategies for improving transformation efficiency were tested.

Optimal kanamycin concentrations varied with explant type and cultural conditions. Green shoots were seldom obtained when kanamycin selection was followed immediately after Agrobacterium infection. A 7–10 day recovery of treated explants before kanamycin selection was adopted. Our initiation study with kanamycin selection at concentrations of 25 to 50 mg/l had a higher regeneration frequency (15–45%) than other kanamycin concentrations. However less than 20% of the kanamycin-resistant plantlets selected at these concentrations proved to be positive for NPT II activity. In addition, only 9.7% of plantlets surviving the 25 mg/l kanamycin selection and 28.6% from the 50 mg/l kanamycin selection contained both the NPT II and ipt genes, as determined by PCR. Considering all relevant criteria, an optimal concentration of 75 mg/l kanamycin was used for selecting plantlets. At this concentration, the transformation frequency varied from 0.6 to 12.8%, depending on the type of culture explant and culture conditions (Tables 1 and 2). Over two hundred kanamycin resistant ($Km^R$) plantlets were recovered. Table 1 summarizes the effects of seedling ages and explant type on the frequency of shoot regeneration, and Table 2 summarizes the effect of various co-culture conditions on transformation efficiency in peduncle.

TABLE 1

| Seedling ages or storage time | 3 days after in vitro germination | | 9 days after in vitro germination | | 2–3 weeks after harvest[a] |
| --- | --- | --- | --- | --- | --- |
| Explants | Cotyledon | Hypocotyl | Cotyledon | Hypocotyl | Peduncle |
| Transformation frequency (%)[b] | 16/288 (5.6) | 45/306 (14.7) | 6/124 (4.8) | 27/361 (7.5) | 44/380 (11.6) |
| No. of plantlets recovered[c] | 31 | 65 | 11 | 46 | 372 |
| # with positive NPTII activity (%) | 20/31 (64.5) | 34/65 (52.3) | 6/11 (54.5) | 20/46 (43.5) | 264/372 (71.0) |

[a]flower heads were harvested 2 weeks after bolting and stored at 4° C. before use
[b]# of regenerable explants/total # inoculated explants
[c]recorded 3 months after kanamycin selection at 75 mg/l.

TABLE 2

| Co-cultural conditions | Co-cultured under light | | | Co-cultured under dark | | |
| --- | --- | --- | --- | --- | --- | --- |
| | Nursed[a] | Non-nursed | Total | Nursed | Non-nursed | Total |
| Transformation frequency (%)[b] | 12/94 (12.8) | 10/80 (12.5) | 22/174 (12.6) | 3/90 (3.3) | 2/78 (2.6) | 5/168 (3.0) |
| No. $Km^R$ Plants[c] | 133 | 134 | 267 | 149 | 125 | 274 |
| % positive NPTII activity | 39.8 | 61.2 | 50.6 | 69.1 | 56.0 | 63.1 |

[a]nursed with 2–3 ml of 6 to 8-day old tobacco suspension cells
[b]# regenerable explants/total # infected explants
[c]# green shoot recorded 3 months after kanamycin selection at 75 mg/l It was found that peduncle (flower stalk) excised from the floret head had a more stable transformation rate. Peduncle stored at 4° C. could be used even 2–4 weeks after harvest. However, prolonged storage did lead to a decline in regeneration frequency. Transformants were also obtained from the infection of hypocotyl and cotyledon segments.

As indicated in Tables 1 and 2, transformation frequency varied according to the type and age of the explant (Tables 1 and 2). Hypocotyl and Cotyledon explants from 3-day old seedlings led to better transformation frequencies than that of 9-day old seedlings. The rationale for choosing 3-day old seedling will be discussed later below.

Comparisons between vacuum-aided infiltration and direct co-incubation were evaluated using pooled data from at least 4 individual tests. Transformation frequencies in peduncle explants were 23.2% (39/168) and 16.6% (29/175) for vacuum-aided and direct soak procedures, respectively, using 50 mg/l kanamycin selection. Vacuum-aided infiltration had a slight advantage over the direct soaking method in peduncle explants, but not in seedling explants, due to a poor survival rate of seedling tissue using this method. In peduncle infections, it was found that co-culture in light resulted in a higher transformation frequency (12.6%) than co-culture in dark (3.0%) (Table 2). The effect of nursing on transformation efficiency was not significant. A comparison of the transformation frequency using pSG529(+) versus pSG766A as delivery vehicle was also performed. It was found that pSG766A had a higher transformation frequency and higher percentage of NPT II positive transformants than pSG529(+) (Table 3). Table 3 summarizes the data for the use of both plasmid delivery vehicles.

mation. Generally, only NPT II positive plantlets were transferred to the growth chamber and further subjected to PCR for confirmation of NPT II and ipt inserts. The pre-screening using dot blotting indicated that, on average, over 50% of $Km^R$ plantlets were positive for NPT II. PCR analysis then indicated that over 60% of the dot blot-positive samples were also positive for NPT II and ipt sequences by PCR. Analysis by PCR also revealed that some plantlets with negative NPT II dot blots were nevertheless positive for NPT II by PCR. In a total of 38 $Km^R$, NPT II activity-negative plantlets, 25 plants were PCR positive for both NPT II and ipt genes (Table 4). Table 4 summarizes the screening results using NPT II dot blotting and PCR.

TABLE 4

|  | NPT II positive | | | NPT II negative | | |
| --- | --- | --- | --- | --- | --- | --- |
| PCR Genotype | pSG529(+) | pSG766A | Total | pSG529(+) | pSG766A | Total |
| NPT II(+), ipt(+) | 13/20[a] | 38/63 | 51/83 | 8/12 | 17/26 | 25/38 |
| (%) | (65.0) | (60.3) | (61.4) | (66.7) | (65.4) | (65.8) |
| NPT II(−), ipt(+) | 1/20 | 9/63 | 10/83 | 0/12 | 2/26 | 2/38 |
| (%) | (5.0) | (14.3) | (12.0) | (0.0) | (7.7) | (5.3) |
| NPT II(+), ipt(−) | 2/20 | 9/63 | 11/83 | 1/12 | 3/26 | 4/38 |
| (%) | (10.0) | (14.3) | (13.3) | (8.3) | (11.5) | (10.5) |
| NPT II(−), ipt(−) | 4/20 | 7/63 | 11/83 | 3/12 | 4/26 | 7/38 |
| (%) | (20.0) | (11.1) | (13.3) | (25.0) | (15.4) | (18.4) |
| Total | 32 | 89 | 121 | 12 | 26 | 38 |

[a]indicated as # plantlets with particular inserted DNA fragment/# regenerated plants assayed Gene silencing was observed among some transformants, which was confirmed by Southern hybridization. In most cases, the $Km^R$ plants showed no deterioration or morphological alternations relative to control plants without a transgene.

Nuclear DNA Phase of Explants and Ploidy of Transformants. Initially, explants were derived from the hypocotyl and cotyledon of 8 to 12 day-old seedlings. However, the transformation frequency of 8–12 day post-germination hypocotyl without any pre-culture was not very stable (0–19.3%). In contrast, explants from peduncle had a steady transformation rate (5.4% to 10.7%) even after storage and without preculture.

By examining the nuclear DNA phase of seeding explants (cotyledon and hypocotyl) from days 2–12 after germination, distinct patterns or populations of cells with a particular nuclear DNA phase were seen from day 2 to day 4 post-germination. Over 4 days after germination the nuclear DNA phase populations, although variable, consistently exhibited four major DNA peaks (2C, 4C, 8C, and 16C) in hypocotyl and three peaks (2C, 4C, 8C) in cotyledon. At days 2–3 after germination, 2C, 4C, and 8C peaks were apparent in hypocotyl, while only 2C and 4C peaks were seen in cotyledon. After 4 days post-germination, additional 8C and 16C peaks became prominent in cotyledon and hypocotyl explants, respectively.

As discussed above, a comparison of the transformation frequencies of explants at 3 days (Age 3) and 9 days (Age 9) post-germination indicated that a higher transformation frequencies in Age 3 explants than in Age 9 explants (Table 1) without preculture. The nuclear DNA phases of Age 3 and Age 9 hypocotyl and cotyledon are shown in FIGS. 2A–2D. Higher transformation frequencies were noted in hypocotyl than in cotyledon.

The nuclear DNA phases of peduncle explants were also examined. Explant segments excised right beneath the flower head had nuclear DNA phase populations of 2C and

TABLE 3

| Plasmid | pSG529(+) | | | |
| --- | --- | --- | --- | --- |
| Explants | Cotyledon | Hypocotyl | Peduncle | Total |
| Transformation frequency (%)[a] | 1/81 (1.2) | 1/156 (0.6) | 9/171 (5.3) | 11/408 (2.7) |
| % positive NPTII activity[b] | 25.0 (1/4) | 33.3 (1/3) | 44.3 (58/131) | 43.5 (60/138) |
| Plasmid | pSG766A | | | |
| Explants | Cotyledon | Hypocotyl | Peduncle | Total |
| Transformation frequency[a] | 4/156 (2.5%) | 10/175 (5.7%) | 18/171 (10.5%) | 32/502 (6.4%) |
| % positive NPTII activity[b] | 36.7 (11/30) | 33.9 (20/59) | 61.0 (250/410) | 56.3 (281/499) |

Figure 2A:
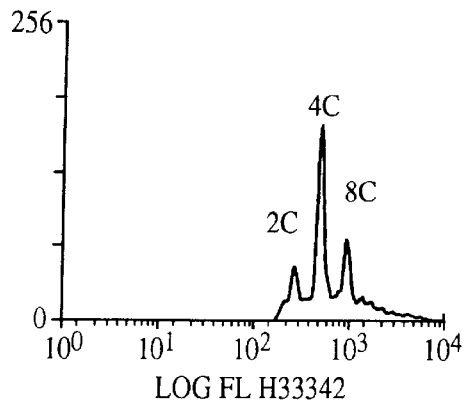
FIGS. 2A–2F are histograms of nuclear DNA content versus cell number. The X axis is the logarithmic integrated fluorescence of bis-benzimide (Hoechst 33342), and the Y axis is number of events. Scales are standardized for ease of comparison.
Figure 2B:
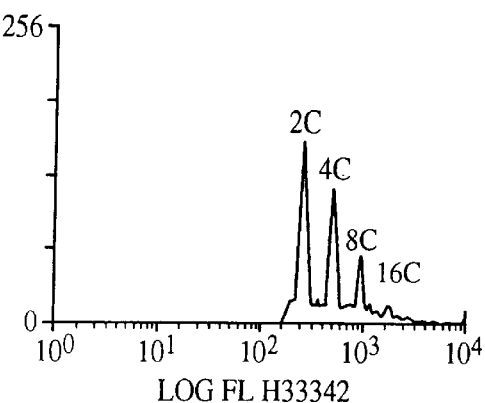
Figure 2C:
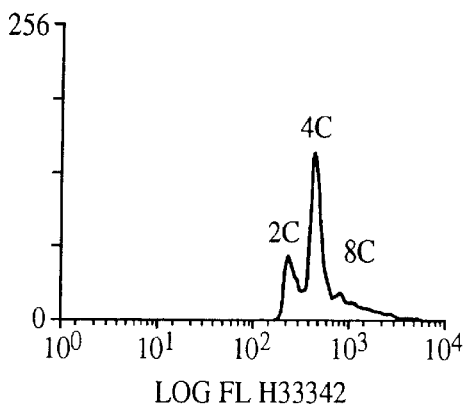
Figure 2D:
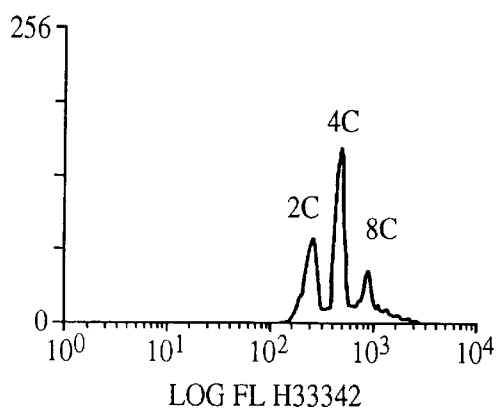
Figure 2E:
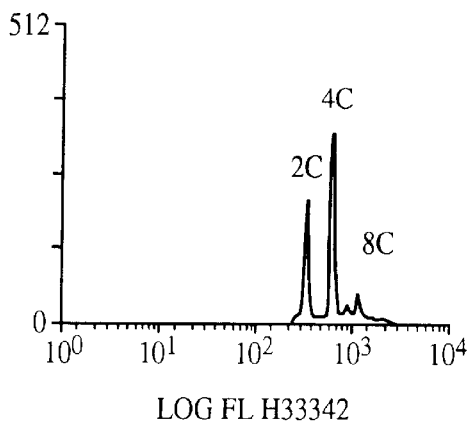
Figure 2F:
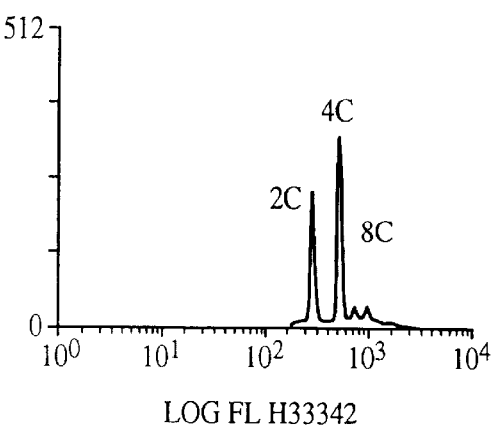

[a]indicated as # regenerable explants/total # infected explants
[b]values within parentheses indicated # positive plantlets/total # $Km^R$ plants screened Confirmation of Transformation. Primary plantlets regenerated from kanamycin selection were first subjected to an NPT II activity assay via dot hybridization. The NPT II activity served as an initial indicator of successful transfor- 4C, but the 8C peak was not significant even after storage at 4° C. over several weeks (FIGS. 2E and 2F). As the distance between the segments and the flower head above increased, the proportions of 4C and 8C cells increased. Peduncle explants with a relatively higher proportion of cells having a nuclear DNA content of 4C and a relatively lower proportion of cells having a nuclear DNA content of greater than 4C have a higher regeneration ability and transformation rate. In addition, storage of flower heads at 4° C. sometimes increased the proportion of 8C cells. Thus, it was discovered that plant cell populations with a higher proportion of 4C cells and a lower proportion of cells having greater than 4C nuclear DNA were surprisingly suitable for transformation and regeneration of plants. Indeed, the use of Age 3 hypocotyl and stored peduncles for transformation without any preculture was highly reproducible.

Ploidy levels of the transformants were also determined by measuring the nuclear DNA content via flow cytometry. Both diploids and tetraploids were found in cotyledon and hypocotyl, as well as in peduncle. The percentage of tetraploids in cotyledon, peduncle, and hypocotyl transformations were 6.7, 17.4, and 35%, respectively (Table 5). Table 5 summarizes the ploidy levels of transgenic plants obtained from different explant sources.

TABLE 5

| | Plant ploidy levels | | |
|---|---|---|---|
| Explant types | 2n | 4n | Total |
| Cotyledon (%) | 14 (93.3) | 1 (6.7) | 15 |
| Hypocotyl (%) | 13 (65.0) | 7 (35.0) | 20 |
| Peduncle (%) | 109 (82.6) | 23 (17.4) | 132 |
| Total (%) | 136 (81.4) | 31 (18.6) | 167 |

Delay in Transformed Broccoli Florets. At the time of maturation, a flower head and branch, as well as detached leaves were examined for any effect of ipt gene expression after storing at 25° C. for 4 days. The presence of visible yellowing and chlorophyll content were noted. Chlorophyll retention was used as an indicator of delay of yellowing. Pieces of mature leaf were excised from ipt transgenic plants and non-transformed control, and the chlorophyll contents (both chlorophyll a and b) were measured at the day of sampling and 4 days after storage at 25° C. The percent reduction in chlorophyll content at day 4 versus day 0 was quantitated as evidence of yellowing.

A chlorophyll content at day 4 greater than 60% of the initial chlorophyll content at day 0 was considered to be evidence of a delay in yellowing, because the day 4 chlorophyll content of untransformed control plants seldom exceeded 50% of the day 0 amount, with most controls being around 20–30% of control. Out of a total of 171 $Km^R$ plants grown to maturity, 21.6% of the transformants showed a delay in yellowing in leaf, and 10.1% showed a delay in yellowing in the floret head. Only 5 plants (2.9%) were found to postpone yellowing in both detached leaf and floret. Florets showing a delay in yellowing were typically characterized by patches of green and patches of yellow, rather than a random distribution from floret to floret.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. A method of genetically transforming Brassica oleracea cells, the method comprising:

determining, from a plurality of cell populations in a tissue of Brassica oleracea, a cell population containing a higher proportion of cells having a nuclear DNA phase of 4C and a lower proportion of cells having greater than 4C nuclear DNA than that in said tissue;

selecting, from said plurality of cell populations in said tissue, a cell population containing a higher proportion of cells having a nuclear DNA phase of 4C and a lower proportion of cells having greater than 4C nuclear DNA than that in said tissue; and contacting the selected cell population with a bacterium of the genus Agrobacterium to form a mixed culture, the bacterium containing a T-DNA which comprises at least one transgene, thereby producing cells that are stably transformed with said at least one transgene.

2. The method of claim 1, wherein the selected cell population is not precultured.

3. The method of claim 1, further comprising, after the contacting step, subjecting the mixed culture to vacuum pressure.

4. The method of claim 3, wherein the vacuum pressure is 0.1 bar to 0.8 bar.

5. The method of claim 1, wherein the tissue is of a broccoli plant.

6. The method of claim 1, wherein the tissue is of a peduncle.

7. The method of claim 1, wherein the T-DNA further includes a kanamycin resistance gene, and the method further comprises, after the contacting step, selecting for cells in a medium containing kanamycin.

8. The method of claim 7, wherein the medium contains about 25 mg/l or more of kanamycin.

9. The method of claim 8, wherein the medium contains about 50 to 100 mg/l of kanamycin.

10. The method of claim 9, wherein the medium contains about 75 mg/l of kanamycin.

11. The method of claim 1, wherein the selecting step includes removing cells having a nuclear DNA phase of greater than 4C from the selected cell population.

12. A method of genetically transforming Brassica oleracea cells, the method comprising;

determining, from a plurality of cell populations in a tissue of Brassica oleracea, a cell population containing the highest proportion of cells having a nuclear DNA phase of 4C and a lower proportion of cells having greater than 4C nuclear DNA than that in said tissue;

selecting, from said plurality of cell populations in said tissue, a cell population containing the highest proportion of cells having a nuclear DNA phase of 4C and a lower proportion of cells having greater than 4C nuclear DNA than that in said tissue; and contacting the selected cell population with a bacterium of the genus Agrobacterium to form a mixed culture, the bacterium containing a T-DNA which comprises at least one transgene, thereby producing cells that are stably transformed with said at least one transgene.

13. The method of claim 12, wherein the selected cell population is free of any preculturing.

14. The method of claim 12, further comprising, after the contacting step, subjecting the mixed culture to vacuum pressure.

15. The method of claim 12, wherein the T-DNA further includes a kanamycin resistance gene, and the method further comprises, after the contacting step, selecting for cells in a medium containing kanamycin.

16. The method of claim 12, wherein the tissue is of a broccoli plant.

17. The method of claim 5, wherein the transgene includes a nucleotide sequence encoding an isopentyl transferase.

18. The method of claim 16, wherein the transgene includes a nucleotide sequence encoding an isopentyl transferase.

19. A method of genetically transforming *Brassica oleracea* cells, the method comprising;

determining, from a plurality of cell populations in a tissue of *Brassica oleracea*, a cell population containing a higher proportion of cells having a nuclear DNA phase of 4C and a lower proportion of cells having greater than 4C nuclear DNA than that in said tissue;

selecting, from said plurality of cell populations in said tissue, a cell population containing a higher proportion of cells having a nuclear DNA phase of 4C and a lower proportion of cells having greater than 4C nuclear DNA than that in said tissue; and contacting the selected cell population with a bacterium of the genus Agrobacterium to form a mixed culture, the bacterium containing a T-DNA which comprises at least one transgene, thereby producing cells that are stably transformed with said at least one transgene, wherein the tissue has not been precultured.

20. The method of claim 19, wherein the cells are broccoli cells.

21. A method of genetically transforming *Brassica oleracea* cells, the method comprising;

determining, from a plurality of cell populations in a tissue of *Brassica oleracea*, a cell population containing the highest proportion of cells having a nuclear DNA Phase of 4C and a lower proportion of cells having greater than 4C nuclear DNA than that in said tissue;

selecting, from said plurality of cell populations in said tissue, a cell population containing the highest proportion of cells having a nuclear DNA phase of 4C and a lower proportion of cells having greater than 4C nuclear DNA than that in said tissue; and contacting the selected cell population with a bacterium of the genus Agrobacterium to form a mixed culture, the bacterium containing a T-DNA which comprises at least one transgene, thereby producing cells that are stably transformed with said at least one transgene, wherein the tissue has not been precultured.

22. The method of claim 21, wherein the cells are broccoli cells.

* * * * *